US012646312B2

(12) United States Patent
Nakagomi

(10) Patent No.: US 12,646,312 B2
(45) Date of Patent: Jun. 2, 2026

(54) MEDICAL IMAGE PROCESSING APPARATUS

(71) Applicant: CANON MEDICAL SYSTEMS CORPORATION, Otawara (JP)

(72) Inventor: Keita Nakagomi, Utsunomiya (JP)

(73) Assignee: CANON MEDICAL SYSTEMS CORPORATION, Otawara (JP)

( * ) Notice: Subject to any disclaimer, the term of this patent is extended or adjusted under 35 U.S.C. 154(b) by 257 days.

(21) Appl. No.: 18/457,463

(22) Filed: Aug. 29, 2023

(65) Prior Publication Data

US 2024/0071069 A1     Feb. 29, 2024

(30) Foreign Application Priority Data

Aug. 31, 2022     (JP) ................................. 2022-138396

(51) Int. Cl.
　*G06K 9/00*　　　(2022.01)
　*G06V 10/26*　　　(2022.01)
　　　(Continued)

(52) U.S. Cl.
　CPC ............ *G06V 10/84* (2022.01); *G06V 10/267* (2022.01); *G06V 10/426* (2022.01);
　　　(Continued)

(58) Field of Classification Search
　CPC ......... G06T 7/0012; G06T 2207/30101; G06T 7/12; G06T 7/11; G06T 7/162; G06T 2207/30048; G06T 2207/10081; G06T 2207/10072; G06T 2207/10121; G06T 7/13; G06T 7/62; G06T 7/0014; G06T 7/246; G06T 11/60; G06T 2207/10088; G06T 7/33; G06T 7/155; G06T 2207/20044; G06T 2207/30172; G06T 7/149; G06T 2207/30004; G06T 2210/41; G06T 2207/10101; G06T 2207/20152; G06T 2207/30061; G06T 2207/10064; G06T 17/20; G06T 2207/20072;
　　　(Continued)

(56) References Cited

U.S. PATENT DOCUMENTS

| | | | |
|---|---|---|---|
| 7,953,262 | B2 | 5/2011 | Suryanarayanan et al. |
| 8,315,963 | B2 | 11/2012 | Wiemker et al. |

(Continued)

FOREIGN PATENT DOCUMENTS

| | | |
|---|---|---|
| JP | 2008-188428 A | 8/2008 |
| JP | 2009-539540 A | 11/2009 |
| JP | 2014-61072 A | 4/2014 |

*Primary Examiner* — Alex Kok S Liew
(74) *Attorney, Agent, or Firm* — Oblon, McClelland, Maier & Neustadt, L.L.P.

(57) ABSTRACT

The medical image processing apparatus disclosed herein includes processing circuitry configured to acquire a medical image for setting identification information for identifying a plurality of regions in the medical image, determine a plurality of seed points in the medical image, select one of the plurality of seed points on a shortest path from a first node, the shortest path being a path in which a sum of energies between pixels in the medical image is minimized and the first node being a pixel of the medical image for which the identification information is not set, and allocate the identification information.

13 Claims, 12 Drawing Sheets

(51) Int. Cl.

| | |
|---|---|
| *G06V 10/426* | (2022.01) |
| *G06V 10/764* | (2022.01) |
| *G06V 10/84* | (2022.01) |
| *G16H 30/40* | (2018.01) |

(52) U.S. Cl.
CPC ........... *G06V 10/764* (2022.01); *G16H 30/40* (2018.01); *G06V 2201/03* (2022.01)

(58) Field of Classification Search
CPC . G06T 2207/20101; G06T 2207/30072; G06T 2207/10056; G06T 2207/10132; G06T 2207/20076; G06T 2207/20081; G06T 2207/20161; G06T 2207/30104; G06T 7/181; G06T 7/60; G06T 7/66; G06T 2200/04; G06T 2207/30016; G06T 2207/30024; G06T 2207/30028; G06T 2207/30041; G06T 7/35; G06T 11/008; G06T 2207/20061; G06T 2207/20116; G06T 2207/20168; G06T 2207/30068; G06T 2211/412; G06T 7/168; G06T 7/174; G06T 11/005; G06T 19/00; G06T 2200/08; G06T 2207/10004; G06T 2207/10108; G06T 2207/10116; G06T 2207/20064; G06T 2207/20164; G06T 2207/30021; G06T 2207/30204; G06T 7/10; G06T 7/136; G06T 7/143; G06T 7/64; G06T 7/70; G06T 15/08; G06T 17/00; G06T 2207/10016; G06T 2207/10076; G06T 2207/10104; G06T 2207/10112; G06T 2207/20016; G06T 2207/20021; G06T 2207/20084; G06T 2207/30012; G06T 2207/30064; G06T 5/73; G06T 7/187; G06T 7/194; G06T 7/215; G06T 7/30; G06T 7/337; G06T 7/73; G06T 7/97; G06T 1/0007; G06T 11/003; G06T 15/10; G06T 17/05; G06T 19/003; G06T 19/20; G06T 2207/10096; G06T 2207/20036; G06T 2207/20092; G06T 2207/20096; G06T 2207/20104; G06T 2207/20121; G06T 2207/20124; G06T 2207/20128; G06T 2207/20132; G06T 2207/20156; G06T 2207/20201; G06T 2207/20216; G06T 2207/20224; G06T 2207/30096; G06T 2207/30201; G06T 2219/021; G06T 2219/028; G06T 2219/2012; G06T 3/00; G06T 3/067; G06T 5/94; G06T 7/0016; G06T 7/248; G06T 7/251; G06T 7/254; G06T 7/38; G06T 7/46; G06T 7/55; G06T 7/74; A61B 6/504; A61B 6/12; A61B 6/481; A61B 6/503; A61B 6/5247; A61B 6/5217; A61B 34/10
See application file for complete search history.

(56) References Cited

U.S. PATENT DOCUMENTS

| | | | |
|---|---|---|---|
| 9,355,458 B2 | 5/2016 | Ihara | |
| 2007/0286483 A1* | 12/2007 | Delong .................... | G06T 7/12 |
| | | | 382/173 |
| 2008/0188962 A1 | 8/2008 | Suryanarayanan et al. | |
| 2009/0177444 A1 | 7/2009 | Wiemker et al. | |
| 2015/0187085 A1* | 7/2015 | Ihara ........................ | G06T 7/12 |
| | | | 382/128 |

* cited by examiner

1: MEDICAL IMAGE
   PROCESSING SYSTEM

10

MEDICAL IMAGE
DIAGNOSTIC APPARATUS

20

MEDICAL IMAGE
STORAGE APPARATUS

30

MEDICAL IMAGE
PROCESSING APPARATUS

Start point
(source node)

Seed points

Label 1

Label 2

Label 3

Start point
(source node)

Seed points

Label 1

Label 2

Label 3

MEDICAL IMAGE PROCESSING APPARATUS

CROSS REFERENCE TO RELATED APPLICATIONS

This application is based upon and claims the benefit of priority from the prior Japanese Patent Application No. 2022-138396, filed on Aug. 31, 2022, the entire contents of which are incorporated herein by reference.

FIELD

The embodiments disclosed in the specification and drawings relate to a medical image processing apparatus.

BACKGROUND

In general, in a medical field, when performing diagnosis by using a medical image acquired by a medical image diagnostic apparatus such as an X-ray CT apparatus, a user may use information such as an area, a volume, and a dimension of each region such as an organ, a blood vessel, and a bone imaged in the medical image for diagnosis. In a case where the information such as the area of each region imaged in the medical image is used, the user is required to extract a necessary region in the medical image. However, in a case where the user manually performs the work of extracting the region, a large amount of effort is required for the user.

In recent years, a technique of automatically or semi-automatically extracting a necessary region in a medical image has been proposed in order to reduce effort of a user for the work of extracting this region. Specifically, by performing image processing such as binarization processing or graph cut processing on the medical image, it is possible to extract one region such as a liver in the medical image.

However, in a case where a plurality of regions in an imaging site of a subject such as a plurality of organs in an abdomen of the subject, a plurality of vertebral bodies in a spine, and a cerebral artery and a cerebral vein in a brain are extracted by using the image processing such as binarization processing and graph cut processing, it is necessary to perform calculation for each region and processing of extracting the plurality of regions, and thus, a large amount of time is required for the image processing. Therefore, it is desired to enable region extraction with a plurality of labels to be performed in a short time.

DETAILED DESCRIPTION

With reference to the drawings below, embodiments of a medical image processing apparatus will be described. In the description below, same reference signs are given for components substantially identical in terms of configuration and function, and duplicate description will be given only when necessary.

Figure 1:
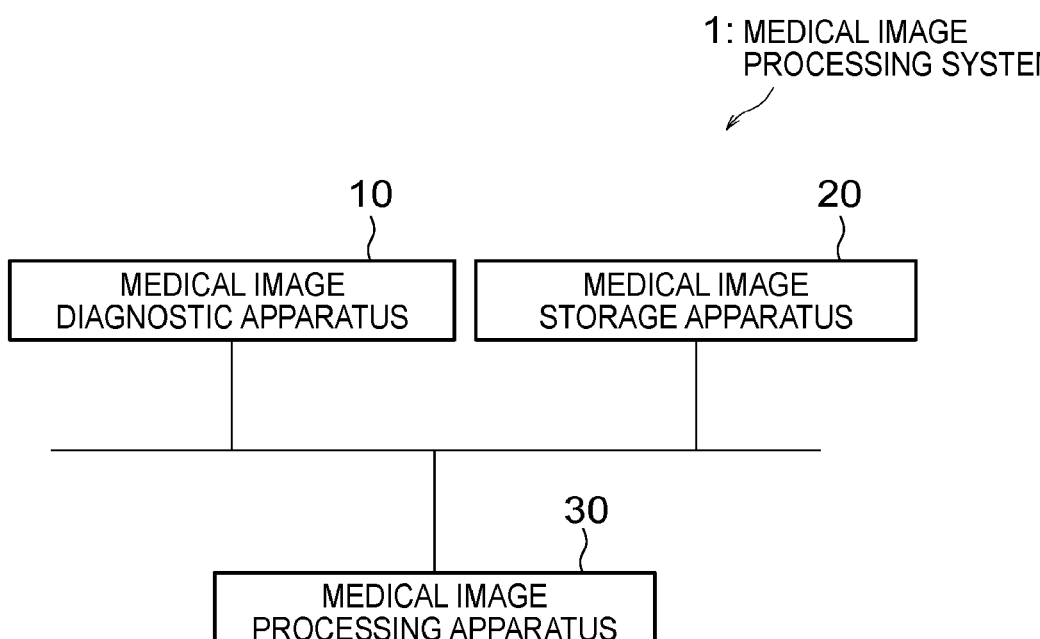
FIG. 1 is a block diagram illustrating an example of a configuration of a medical image processing system according to an embodiment.

FIG. 1 is a block diagram illustrating an example of a configuration of a medical image processing system according to an embodiment. As illustrated in FIG. 1, a medical image processing system 1 according to the present embodiment includes a medical image diagnostic apparatus 10, a medical image storage apparatus 20, and a medical image processing apparatus 30. The medical image diagnostic apparatus 10, the medical image storage apparatus 20, and the medical image processing apparatus 30 are communicably connected via an in-hospital network by a dedicated line in a hospital.

Note that the medical image diagnostic apparatus 10, the medical image storage apparatus 20, and the medical image processing apparatus 30 may be communicably connected to each other via a network via a public line such as the Internet. In addition, the medical image processing apparatus 30 according to the present embodiment is configured separately from the medical image diagnostic apparatus 10, but the medical image processing apparatus 30 may be configured integrally with the medical image diagnostic apparatus 10.

The medical image diagnostic apparatus 10 images a subject and acquires a medical image. Then, the medical image diagnostic apparatus 10 transmits the medical image to the medical image storage apparatus 20 or the medical image processing apparatus 30 via the in-hospital network. For example, the medical image diagnostic apparatus 10 is an X-ray computed tomography (CT) apparatus, a magnetic resonance imaging (MRI) apparatus, or the like. In the following description, a case where the medical image diagnostic apparatus 10 is an X-ray CT apparatus, and the medical image is a CT image of an abdomen of the subject acquired by the X-ray CT apparatus will be described as an example.

The medical image storage apparatus 20 stores medical images acquired by the medical image diagnostic apparatus 10, various images generated by the medical image processing apparatus 30, and the like. In addition, the medical image storage apparatus 20 transmits the CT image, various images, and the like to the medical image diagnostic apparatus 10 or the medical image processing apparatus 30 via the in-hospital network. For example, the medical image storage apparatus 20 is an image server such as a picture archiving and communication system (PACS). In addition, the medical image storage apparatus 20 may be realized by a server group (cloud) connected to the medical image processing system 1 via the network.

The medical image processing apparatus 30 performs various types of information processing related to the subject. Specifically, the medical image processing apparatus 30 executes various types of image processing such as image processing for setting identification information for identifying a plurality of regions in a CT image that is a medical image acquired by the medical image diagnostic apparatus 10 or a CT image transmitted from the medical image storage apparatus 20. For example, the medical image processing apparatus 30 is realized by a computer device such as a server or a workstation.

Here, the identification information is information for identifying a plurality of regions in the CT image, and is, for example, a label or the like classified for each organ. In addition, setting the identification information means, for example, setting labels of different modes for each region, for example, labels of different colors, different shades, different hatching patterns, and the like for each region in order to identify the plurality of regions in the CT image.

Furthermore, the plurality of regions in the CT image, for example, includes an anatomical structure of a human body. The anatomical structure of the human body is, for example, a structure that constitutes a subject such as organs such as a heart or a liver, bones, and blood vessels such as arteries and veins. In addition, this region may be a region including a part of the anatomical structure of the human body, or may be a region including the entire anatomical structure of the human body.

Figure 2:
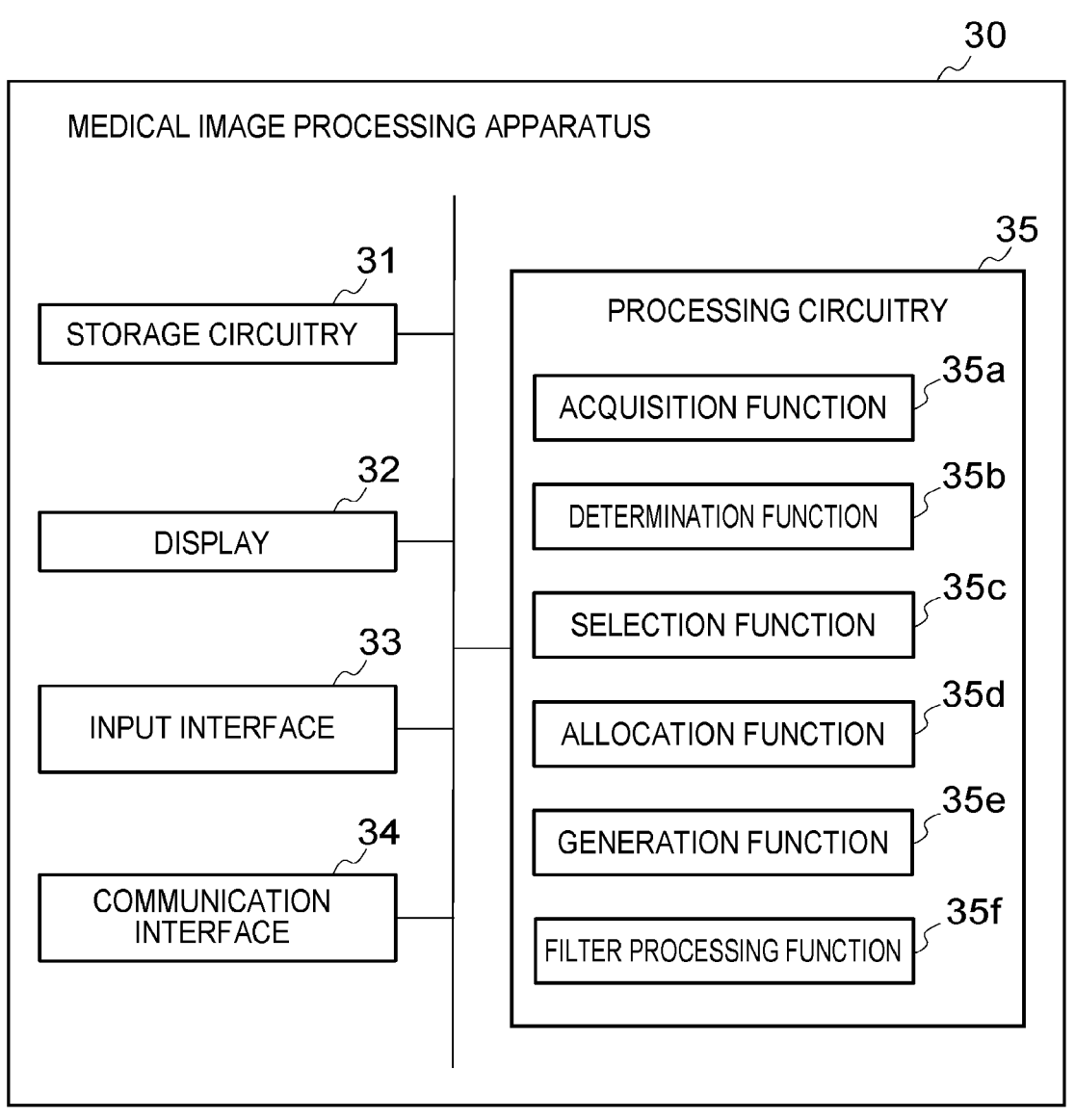
FIG. 2 is a block diagram illustrating an example of a configuration of a medical image processing apparatus according to the embodiment.

FIG. 2 is a block diagram illustrating an example of a configuration of the medical image processing apparatus 30 according to the present embodiment. As illustrated in FIG. 2, the medical image processing apparatus 30 according to the present embodiment includes a storage circuitry 31, a display 32, an input interface 33, a communication interface 34, and a processing circuitry 35.

The storage circuitry 31 is realized by, for example, a random access memory (RAM), a semiconductor memory element such as a flash memory, a hard disk, an optical disk, or the like. In the present embodiment, the storage circuitry 31 stores, for example, various types of information such as a CT image acquired by the medical image diagnostic apparatus 10, a CT image transmitted from the medical image storage apparatus 20, and various images generated by the medical image processing apparatus 30.

The display 32 displays various images and information. For example, the display 32 displays a graphical user interface (GUI) or the like for receiving various operations from the user. In the present embodiment, the display 32 is configured by, for example, a liquid crystal display, a cathode ray tube (CRT) display, or the like.

The input interface 33 receives various input operations from the user, converts the received input operations into electrical signals, and outputs the electrical signals to the processing circuitry 35. The input interface 33 is realized by, for example, a mouse, a keyboard, a trackball, a manual switch, a foot switch, a button, a joystick, a touch pad that performs an input operation by touching an operation surface, a touch screen in which a display screen and the touch pad are integrated, a non-contact input interface using an optical sensor, a voice input interface, and the like. Note that, in the present specification, the input interface 33 is not limited to one including physical operation components such as a mouse and a keyboard. For example, an electric signal processing circuitry that receives an electric signal corresponding to an input operation from an external input device provided separately from the apparatus and outputs the electric signal to the control circuitry is also included in the example of the input interface 33.

The communication interface 34 implements various information communication protocols according to the form of the in-hospital network. The communication interface 34 realizes communication with other apparatuses via the in-hospital network according to the various protocols. In the present embodiment, the medical image processing apparatus 30 is connected to the in-hospital network via the communication interface 34, and communication with the medical image diagnostic apparatus 10 or the medical image storage apparatus 20 is realized.

The processing circuitry 35 is an arithmetic circuitry that performs various calculations, and includes, for example, a processor such as a CPU or a GPU. The processing circuitry 35 according to the present embodiment acquires a CT image from the medical image diagnostic apparatus 10 or the medical image storage apparatus 20, determines a plurality of seed points in the CT image, or allocates identification information to pixels of the CT image, for example.

Therefore, the processing circuitry 35 according to the present embodiment has an acquisition function 35a, a determination function 35b, a selection function 35c, an allocation function 35d, a generation function 35e, and a filter processing function 35f. The acquisition function 35a corresponds to an acquisition unit according to the present embodiment, the determination function 35b corresponds to a determination unit according to the present embodiment, the selection function 35c corresponds to a selection unit according to the present embodiment, the allocation function 35d corresponds to an allocation unit according to the present embodiment, the generation function 35e corresponds to a generation unit according to the present embodiment, and the filter processing function 35f corresponds to a filter processing unit according to the present embodiment.

In the embodiment illustrated in FIG. 2, each processing function performed by the acquisition function 35a, the determination function 35b, the selection function 35c, the allocation function 35d, the generation function 35e, and the filter processing function 35f is stored in the storage circuitry 31 in the form of a program executable by a computer. The processing circuitry 35 is a processor that realizes a function corresponding to each program by reading and executing the program from the storage circuitry 31. In other words, the processing circuitry 35 in a state of reading each program has each function illustrated in the processing circuitry 35 of FIG. 2. Note that, in FIG. 2, it has been described that the acquisition function 35a, the determination function 35b, the selection function 35c, the allocation function 35d, the generation function 35e, and the filter processing function 35f are implemented by a single processing circuitry 35, but these functions may be implemented by combining a plurality of independent processors to configure the processing circuitry 35 and executing a program with each processor.

Figure 3:
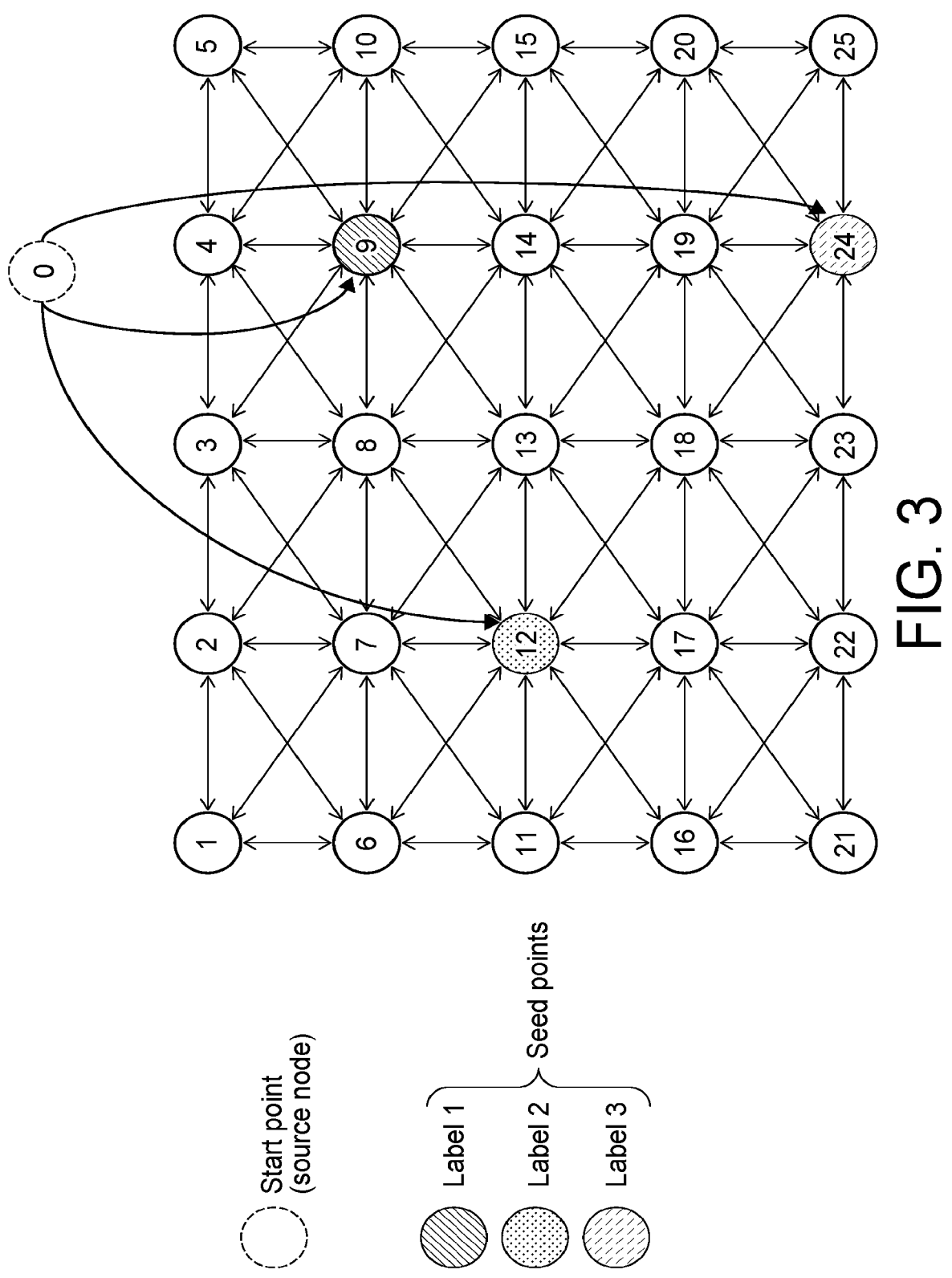
FIG. 3 is a diagram illustrating an example of region extraction in a CT image executed in the medical image processing apparatus according to the embodiment.
Figure 4:
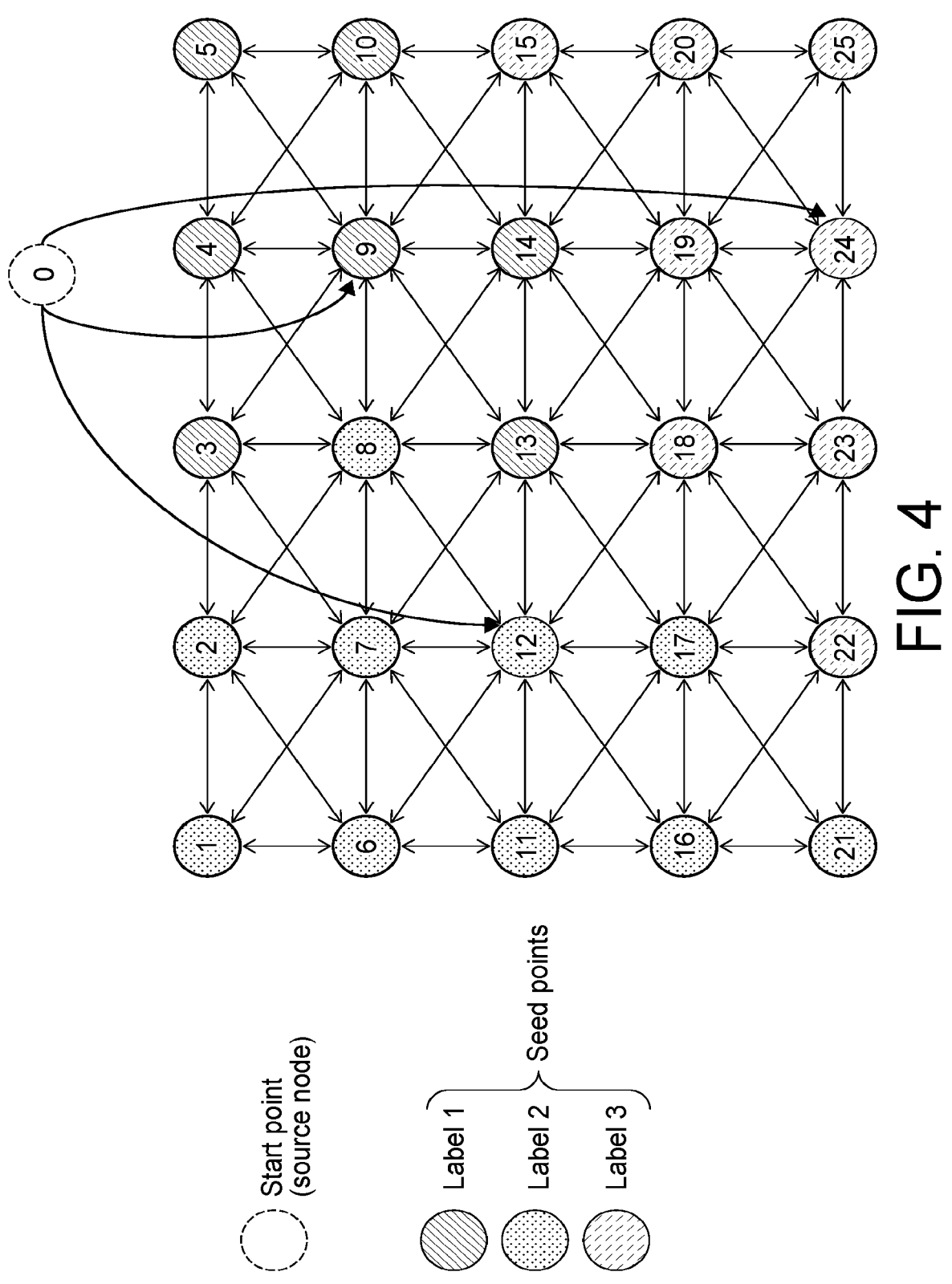
FIG. 4 is a diagram illustrating an example of the region extraction in the CT image executed in the medical image processing apparatus according to the embodiment.

FIGS. 3 and 4 are diagrams illustrating an example of region extraction in a CT image executed in the medical image processing apparatus 30 according to the present embodiment. As illustrated in FIGS. 3 and 4, the medical image processing apparatus 30 generates a graph structure including a plurality of pixels in which different labels are set, performs search for a shortest path with a Dijkstra method once in the graph structure, thereby labeling pixels in which labels are not set, and performs region extraction with a plurality of labels in the CT image.

Here, the Dijkstra method is an algorithm for solving a shortest path problem based on graph theory. With this Dijkstra method, the shortest path between two vertices on the graph can be efficiently selected. In the present embodiment, an example of using a path search method based on the Dijkstra method is illustrated, but the path search method is not limited thereto. That is, the path search method used for region extraction is arbitrary.

An example of the graph structure illustrated in FIG. 3 will be described in detail. The CT image for which the region extraction is performed includes a plurality of pixels. In the example illustrated in FIG. 3, the CT image includes 25 pixels. Furthermore, in FIG. 3, for convenience of description, numbers 1 to 25 are allocated to each of the 25 pixels. In the following description, a pixel to which a number n is allocated is referred to as a pixel Pn. For example, a pixel to which the number 1 is allocated is referred to as the pixel P1.

Note that, in the example illustrated in FIG. 3, the CT image includes 25 pixels, but the number of pixels included in the CT image is not limited to 25. That is, the number of pixels included in the CT image is arbitrary, and may be 24 or less or 25 or more.

A label is set as identification information for some pixels in the CT image. That is, the graph structure includes a plurality of seed points which are pixels to which labels are set. In the example illustrated in FIG. 3, labels having different hatching patterns are set for three pixels among 25 pixels in the CT image. Specifically, a label 1 indicated by a left-downward oblique line is set to a pixel P9, a label 2 indicated by a dot is set to a pixel P12, and a label 3 indicated by a right-downward oblique broken line is set to a pixel P24. The pixel P9, the pixel P12, and the pixel P24 to which the labels are set are the seed points.

The plurality of seed points is determined in a medical image by the medical image processing apparatus 30, for example. In the present embodiment, the plurality of seed points is determined, for example, by performing threshold processing on a CT value of the CT image based on the CT value of the CT image.

In the present embodiment, the plurality of seed points is determined by performing threshold processing on the CT value of the CT image, but the means for determining the plurality of seed points is not limited thereto. That is, the means for determining the plurality of seed points is arbitrary. For example, the medical image processing apparatus 30 may receive, from the operator, an input operation of determining the plurality of seed points in the CT image and determine the plurality of seed points in the CT image according to the input operation, or may determine the plurality of seed points in the CT image with a learned model machine-learned to determine the plurality of seed points in the CT image by receiving an input of the CT image.

In the example illustrated in FIG. 3, one seed point is provided for each label, but the number of seed points provided for each label is not limited to one. That is, the number of seed points provided for each label is arbitrary, and a plurality of seed points may be provided for each label.

In addition, a label is not set as identification information for some pixels in the CT image. That is, the graph structure includes a plurality of first nodes which are pixels to which labels are not set. In the example illustrated in FIG. 3, identification information is not set for pixels other than the pixel P9, the pixel P12, and the pixel P24 in the CT image. The pixels other than the pixel P9, the pixel P12, and the pixel P24 to which the label is not set are the first nodes.

The graph structure includes a start point provided outside the CT image. In the example illustrated in FIG. 3, a start point to which a number 0 is allocated is provided outside the image of the CT image. This start point corresponds to a second node in the present embodiment.

The graph structure includes a plurality of first edges connecting the plurality of seed points and the plurality of first nodes. Energy is applied to each of the first edges. The energy applied to each first edge is applied based on, for example, a difference between pixels in the CT image. Here, the energy applied based on the difference between the pixels in the CT image is, for example, energy applied based on a difference in pixel values between the pixels in the CT image. That is, the medical image processing apparatus 30 applies energy to the plurality of first edges based on the difference in the pixel values between the pixels in the CT image. For example, the medical image processing apparatus 30 applies energy to the first edge based on the difference in the pixel values between the pixels in the CT image such that the smaller the difference in the pixel values between the pixels in the CT image, the lower the energy applied to the first edge. Here, the pixel value indicates a luminance value of a pixel in a case of a grayscale image, and indicates a property of the pixel such as a luminance value, hue, and saturation of the pixel in a case of a color image. In the example illustrated in FIG. 3, for example, in a case where energy is applied to the first edge connecting a pixel P3 as the first node and the pixel P9 as the seed point, the medical image processing apparatus 30 applies energy to the first edge connecting the pixel P3 as the first node and the pixel P9 as the seed point based on a difference between a pixel value of the pixel P3 and a pixel value of the pixel P9.

In the example illustrated in FIG. 3, the energy applied to each first edge is applied based on the difference between the pixels in the CT image. However, the energy applied to each first edge is not limited to the case of being applied based on the difference between the pixels in the CT image. For example, the energy may be applied based on a likelihood related to connections between the pixels.

In the example illustrated in FIG. 3, the energy applied based on the difference between the pixels in the CT image is applied based on the difference in the pixel values between the pixels in the CT image. However, the energy applied based on the difference between the pixels in the CT image is not limited to be based on the difference in the pixel values between the pixels in the CT image. For example, the energy may be applied based on a difference in existence probability between pixels in the CT image, the existence probability being a probability that a pixel belongs to a region. That is, for example, the medical image processing apparatus 30 applies energy to the first edge such that the smaller the difference in the existence probability between the pixels in the CT image, the existence probability being the probability that the pixel belongs to the region, the lower the energy applied to the first edge.

Furthermore, in the example illustrated in FIG. 3, in a case where the same label is set to adjacent pixels, pixels to which the same label is set may not be connected by the first edge. In addition, in a case where the same label is set to adjacent pixels and pixels to which the same label is set are connected by the first edge, the energy applied to the first edge between the pixels to which the same label is set may be set to 0.

In addition, this graph structure includes a plurality of second edges connecting a plurality of seed points with the start point. The same energy is applied to each of the second edges. In the example illustrated in FIG. 3, each of the pixel P9, the pixel P12, and the pixel P24, which are seed points, is connected to the start point by the second edge, respectively. Then, in the example illustrated in FIG. 3, the energy applied to the second edge is, for example, 0.

In the example illustrated in FIG. 3, the energy applied to the second edge is 0, but the energy applied to the second edge is not limited to 0. That is, the energy applied to the second edge is arbitrary.

In the example illustrated in FIG. 3, the same energy is applied to the second edge, but the same energy may not necessarily be applied to the second edge. That is, the medical image processing apparatus 30 may apply different energy to each of the second edges according to each seed point.

Then, the medical image processing apparatus 30 solves the shortest path problem from the start point to the first node with the Dijkstra method in the graph structure, thereby selecting one of the plurality of seed points on the shortest path from the first node, the shortest path being a path in which a sum of energies between the pixels in the CT image is minimized, and performing region extraction in the CT image. Specifically, the medical image processing apparatus 30 selects the shortest path from the second node to the first node so that the sum of the energies applied to the first edge and the second edge from the start point to the first node is minimized, thereby selecting one of the plurality of seed points on the shortest path from the first node and performing region extraction in the CT image.

Note that, in a case where the energy applied to the second edge is the same, the medical image processing apparatus 30 may select the shortest path from the second node to the first node so that the sum of the energies applied to the first edges from the start point to the first node is minimized, thereby selecting one of the plurality of seed points on the shortest path from the first node. That is, in a case where the same energy is applied to the second edge, the energy applied to the second edge may not be taken into consideration in the selection of the shortest path.

Regarding the region extraction in the CT image, specifically, in the example illustrated in FIG. 3, taking the pixel P1 as an example, the medical image processing apparatus 30 solves the shortest path problem from the start point to the first node in each pixel with the Dijkstra method. As a result, in a case where the shortest path from the start point to the first node in the pixel P1 is selected as "start point→pixel P12→pixel P7→pixel P1", the seed points on the shortest path of the first node in the pixel P1 becomes the pixel P12, which is the seed point immediately before the start point, by tracing the path from the pixel P1 to the start point. Therefore, as illustrated in FIG. 4, the medical image processing apparatus 30 allocates the pixel P1 the label 2 set to the pixel P12, which is one of the plurality of seed points on the shortest path from the pixel P1.

Furthermore, in the example illustrated in FIG. 3, taking a pixel P15 as an example, the medical image processing apparatus 30 solves the shortest path problem from the start point to the first node in each pixel with the Dijkstra method. As a result, in a case where the shortest path from the start point to the first node in the pixel P15 is selected as "start point→pixel P24→pixel P19→pixel P15", the seed point on the shortest path of the pixel P15 becomes the pixel P24 which is the seed point immediately before the start point by tracing the path from the pixel P15 to the start point. Therefore, as illustrated in FIG. 4, the medical image processing apparatus 30 allocates the pixel P15 the label 3 set for the pixel P24, which is one of the plurality of seed points on the shortest path from the pixel P15.

As described above, in the example illustrated in FIG. 3, the medical image processing apparatus 30 solves the shortest path problem from the start point to the first node in each pixel with the Dijkstra method, and traces the path to the start point for the first node in each pixel, thereby allocating, to the first node, the label set to the pixel that is the seed point immediately before the start point. As a result, as illustrated in FIG. 4, the medical image processing apparatus 30 allocates all the first nodes in the graph structure the labels 1 to 3, which are the pieces of identification information set to one of the plurality of seed points on the shortest path of each first node and performs region extraction to which a plurality of labels is allocated in the CT image. That is, the medical image processing apparatus 30 can allocate a plurality of labels to the first nodes only by solving the shortest path problem once with the Dijkstra method, and can perform region extraction to allocate a plurality of labels in the CT image.

Figure 5:
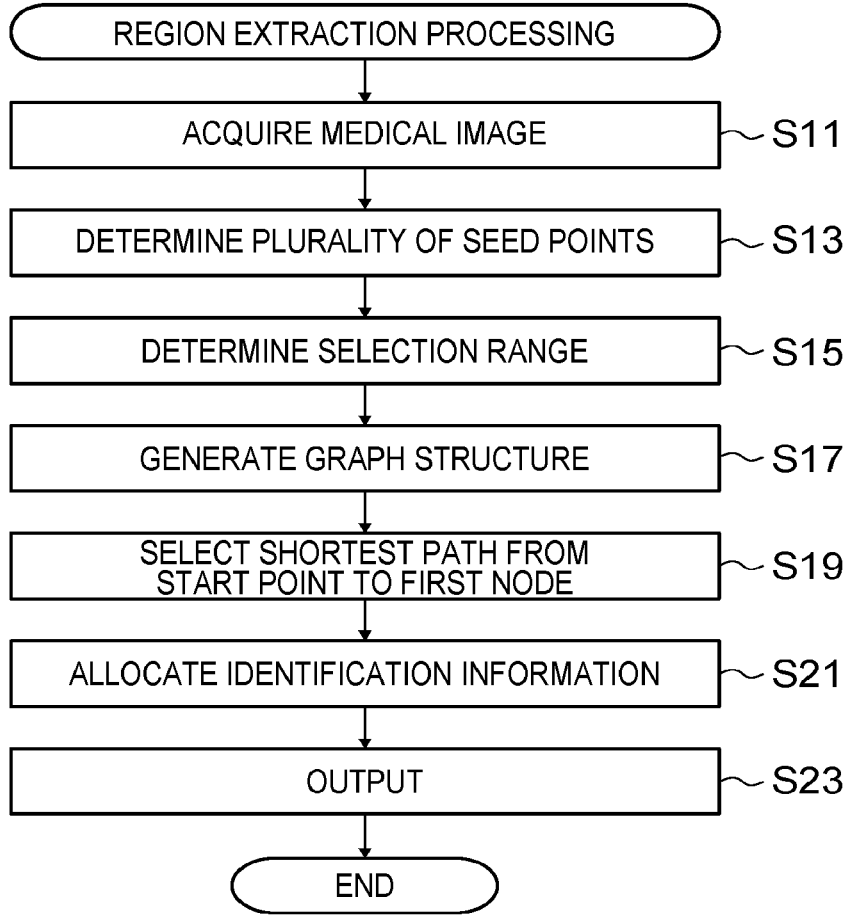
FIG. 5 is a flowchart illustrating contents of region extraction processing executed by the medical image processing apparatus according to the embodiment.

FIG. 5 is a flowchart illustrating the contents of the region extraction processing executed by the medical image processing apparatus 30 according to the present embodiment. In this region extraction processing, a CT image is acquired from the medical image diagnostic apparatus 10 or the medical image storage apparatus 20, a plurality of seed points are determined in the CT image, a graph structure is generated, one of the plurality of seed points on the shortest path, which is a path in which energy is minimized, from the first node is selected, identification information set to the seed point on the shortest path from the first node is allocated based on the selection result, and the CT image for which the region extraction is performed by allocating the identification information is output. For example, this region extraction processing is processing executed when a CT image is acquired from the medical image diagnostic apparatus 10 or the medical image storage apparatus 20.

As illustrated in FIG. 5, first, the medical image processing apparatus 30 acquires a medical image (step S11). The processing of acquiring the medical image is realized by the acquisition function 35a in the processing circuitry 35. Specifically, the medical image processing apparatus 30 acquires the CT image, which is a medical image, from the medical image diagnostic apparatus 10 or the medical image storage apparatus 20 via the communication interface 34.

Figure 6:
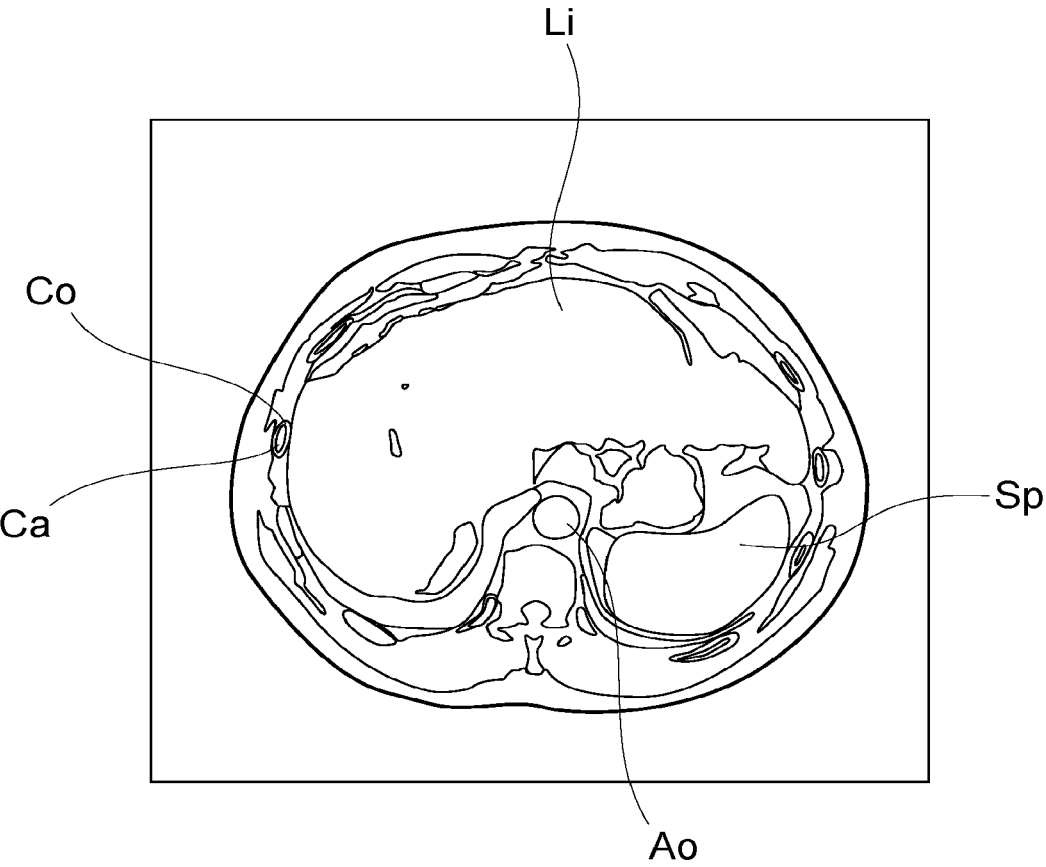
FIG. 6 is a diagram illustrating an example of a CT image acquired by the medical image processing apparatus according to the embodiment.

FIG. 6 is a diagram illustrating an example of the CT image acquired by the medical image processing apparatus 30 according to the present embodiment. As illustrated in FIG. 6, the medical image processing apparatus 30 according to the present embodiment acquires a CT image of an abdomen as the CT image. In the example illustrated in FIG. 6, organs such as a liver Li and a spleen Sp, bones such as a cortical bone Co and a cancellous bone Ca inside the cortical bone Co, and blood vessels such as an aorta Ao are depicted in the CT image of the abdomen.

Next, as illustrated in FIG. 5, the medical image processing apparatus 30 determines a plurality of seed points (step S13). The processing of determining the plurality of seed points is realized by the determination function 35b in the processing circuitry 35. Specifically, in the present embodiment, the medical image processing apparatus 30 performs threshold processing on the CT value of the CT image based on the CT value of the CT image, thereby determining the plurality of seed points.

Figure 7:
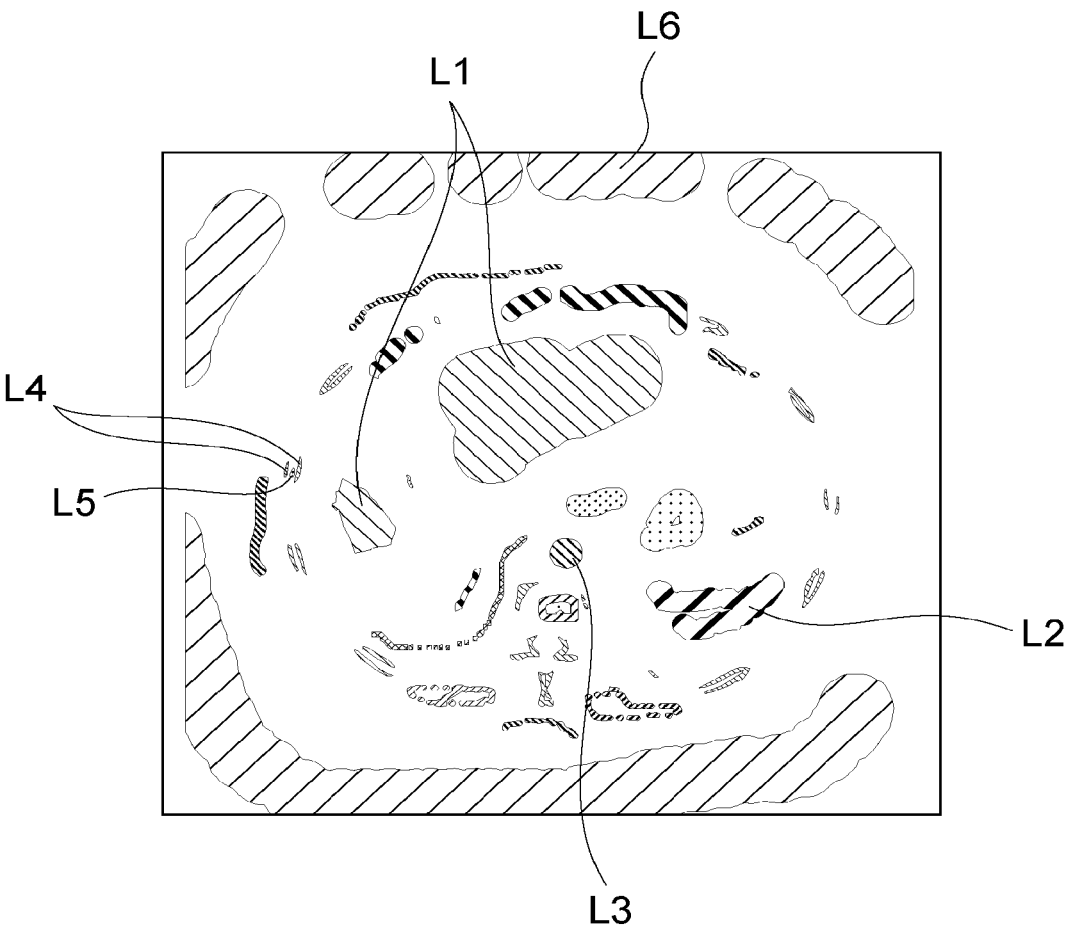
FIG. 7 is a diagram illustrating an example of a plurality of seed points determined by the medical image processing apparatus according to the embodiment.

FIG. 7 is a diagram illustrating an example of the plurality of seed points determined by the medical image processing apparatus 30 according to the present embodiment. As illustrated in FIG. 7, the label that is the identification information set to each of the plurality of seed points has a different hatching pattern for each label. In the example illustrated in FIG. 7, a label L1 is indicated by right-downward thin oblique hatching, a label L2 is indicated by right-upward thick oblique hatching, a label L3 is indicated by right-downward thick oblique hatching, a label L4 is indicated by right-downward thin oblique hatching, a label L5 is indicated by dot-like hatching, and a label L6 is indicated by left-downward thin oblique hatching.

Note that, in the example illustrated in FIG. 7, the medical image processing apparatus 30 sets a label having a different hatching pattern as the identification information for each of the plurality of seed points determined in step S13, but the medical image processing apparatus 30 is not limited to the case of setting a label having a different hatching pattern as the identification information. That is, the label set by the medical image processing apparatus 30 is arbitrary, and for example, the medical image processing apparatus 30 may set a label having a different pixel value or a label having a different color as the identification information for each of the plurality of seed points determined in step S13.

Figure 8:
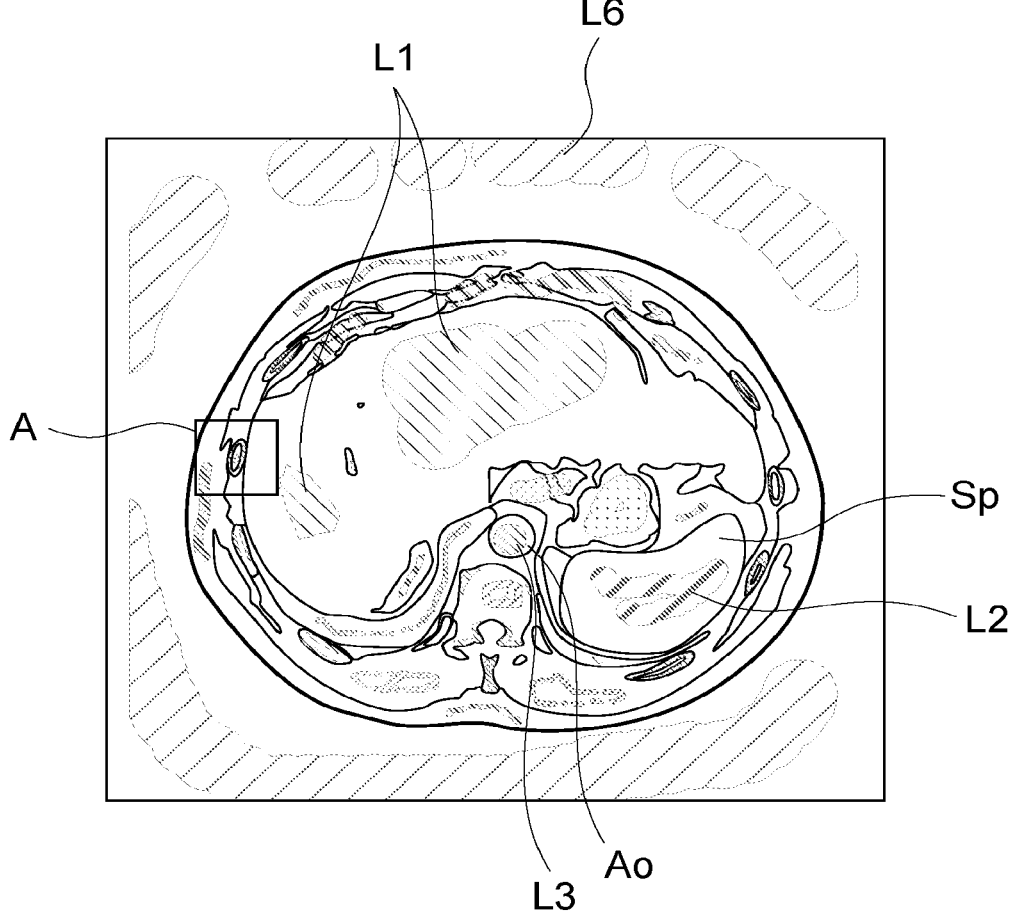
FIG. 8 is a diagram illustrating an example of a CT image for which the plurality of seed points is determined in the medical image processing apparatus according to the embodiment.
Figure 9:
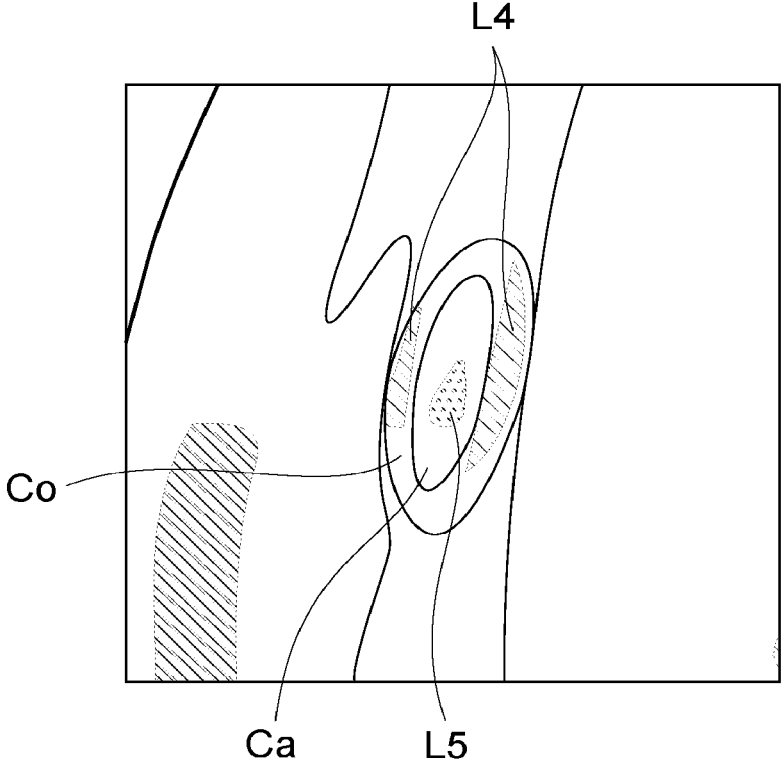
FIG. 9 is an enlarged view of a portion A illustrated in FIG. 8.

FIG. 8 is a diagram illustrating an example of a medical image for which the plurality of seed points is determined in the medical image processing apparatus 30 according to the present embodiment. FIG. 9 is an enlarged view of a portion A illustrated in FIG. 8. As illustrated in FIG. 8, identification information is set in each region of the CT image by determining the plurality of seed points. Specifically, as illustrated in FIG. 8, the label L1 is set in the liver Li, the label L2 is set in the spleen Sp, the label L3 is set in the aorta Ao, and the label L6 is set in an air region outside the human body. In addition, as illustrated in FIG. 9, the label L4 is set in the cortical bone Co, and the label L5 is set in the cancellous bone Ca.

Next, as illustrated in FIG. 5, the medical image processing apparatus 30 determines a selection range (step S15). The processing of determining the selection range is realized by the determination function 35b in the processing circuitry 35. Specifically, the medical image processing apparatus 30 determines, as the selection range, a range to which the identification information is allocated. More specifically, the medical image processing apparatus 30 according to the present embodiment sets all pixels in the medical image as a target range to which identification information is allocated.

Next, as illustrated in FIG. 5, the medical image processing apparatus 30 generates a graph structure (step S17). The processing of generating the graph structure is realized by the generation function 35e in the processing circuitry 35. Specifically, the medical image processing apparatus 30 generates the graph structure in the selection range set in step S15.

More specifically, in the present embodiment, in the CT image acquired in step S11, the medical image processing apparatus 30 sets, as a seed point, a pixel to which a label is set as identification information in step S13, sets, as a first node, a pixel to which a label is not set as identification information, connects a plurality of seed points and a plurality of first nodes by first edges, provides a start point outside the CT image, connects the plurality of seed points to the start point by second edges, applies energy to each first edge, and applies 0 to each second edge as the same energy, thereby generating the graph structure.

Next, as illustrated in FIG. 5, the medical image processing apparatus 30 selects a shortest path from the start point to the first node (step S19). The processing of selecting the shortest path from the start point to the first node is realized by the selection function 35c in the processing circuitry 35. Specifically, the medical image processing apparatus 30 solves the shortest path problem from the start point to the first node in each pixel with the Dijkstra method in the graph structure generated in step S17, thereby selecting the shortest path from the start point to each of the plurality of first node. More specifically, the medical image processing apparatus 30 selects the shortest path from the start point to the first node so that the sum of the energies applied to the first edge and the second edge from the start point to the first node is minimized in the graph structure generated in step S17. As a result, the medical image processing apparatus 30 selects one of the plurality of seed points on the shortest path from the first node.

Next, as illustrated in FIG. 5, the medical image processing apparatus 30 allocates identification information (step S21). The processing of allocating the identification information is realized by the allocation function 35d in the processing circuitry 35. Specifically, the medical image processing apparatus 30 allocates, to the first node, the identification information set to one of plurality of the seed points on the shortest path from the first node based on the selection result selected in step S19.

Figure 10:
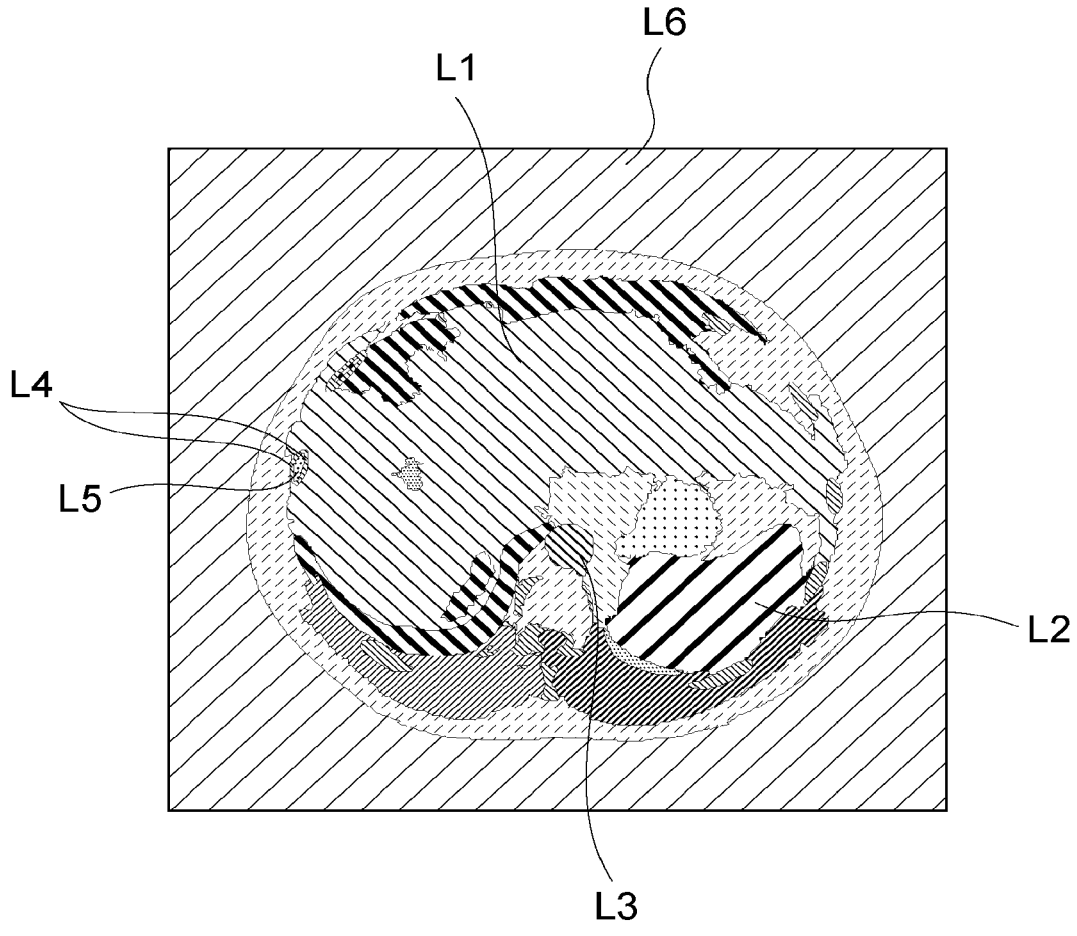
FIG. 10 is a diagram illustrating an example of a case where identification information is allocated to a first node in the medical image processing apparatus according to the embodiment.
Figure 11:
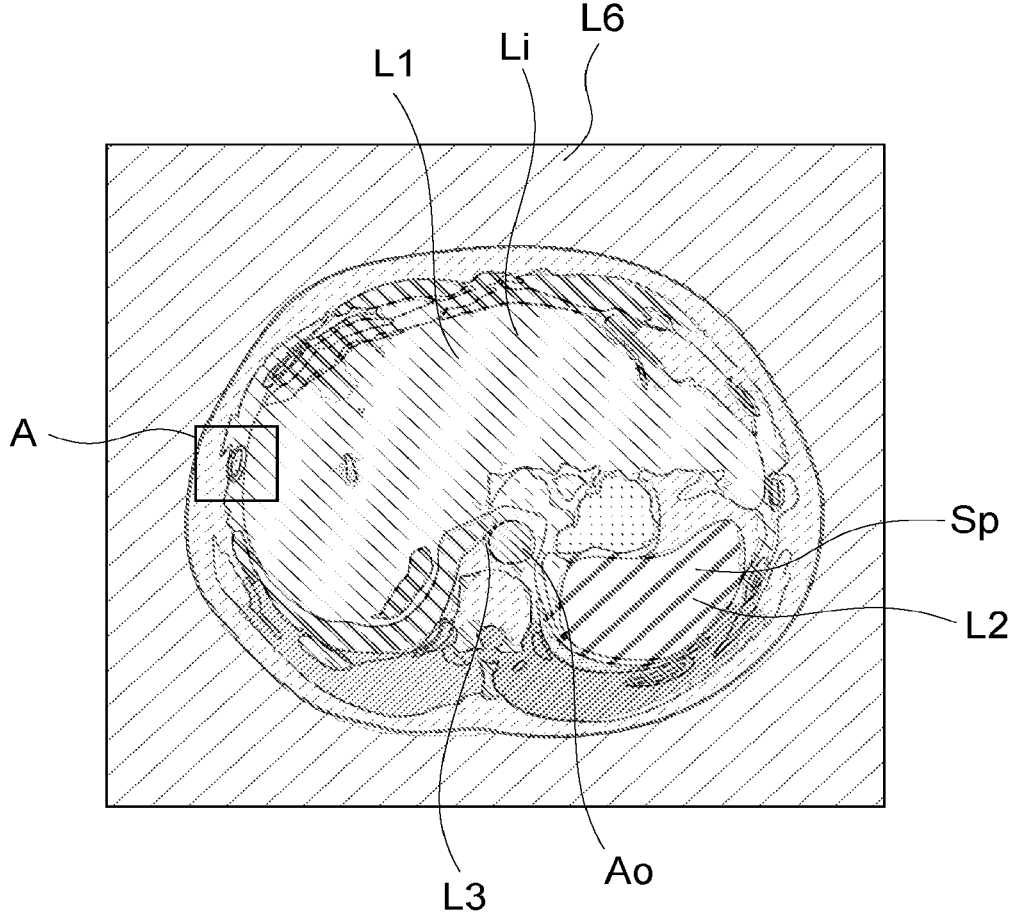
FIG. 11 is a diagram illustrating an example of a case where the identification information is allocated to the first node in the medical image processing apparatus according to the embodiment.
Figure 12:
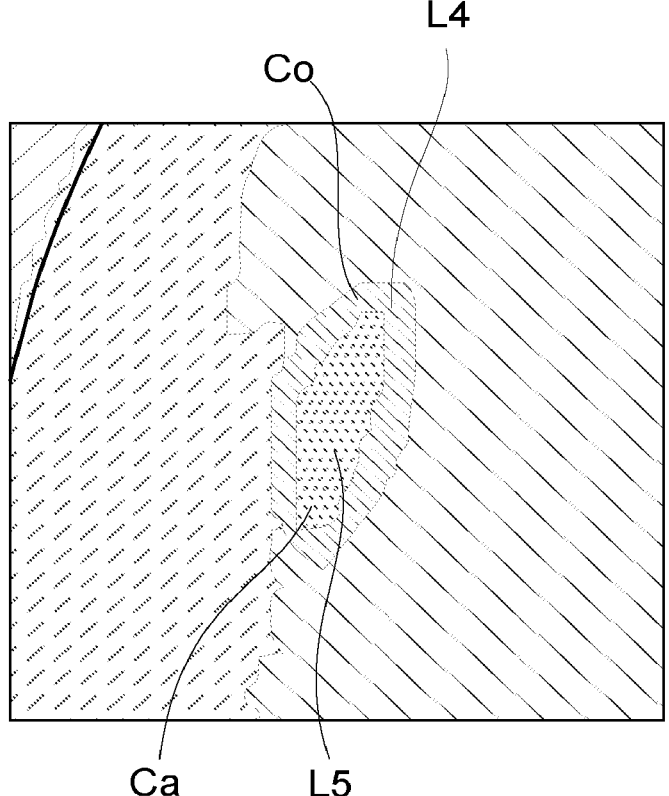
FIG. 12 is an enlarged view of a portion A illustrated in FIG. 11.

FIGS. 10 and 11 are diagrams illustrating an example of a case where identification information is allocated to the first node in the medical image processing apparatus 30 according to the present embodiment. FIG. 12 is an enlarged view of a portion A in FIG. 11. As illustrated in FIG. 10, the medical image processing apparatus 30 according to the present embodiment allocates, to the first node, the identification information set to one of the plurality of seed points on the shortest path from the first node which is the pixel for which the identification information in the CT image is not set. Then, as illustrated in FIG. 11, the label L1 is allocated to the liver Li and the first nodes in the vicinity thereof. In addition, the label L2 is allocated to the spleen Sp and the first nodes in the vicinity thereof. The label L3 is allocated to the aorta Ao and the first nodes in the vicinity thereof. The label L6 is allocated to the first node in the air region outside the human body. In addition, as illustrated in FIG. 12, the label L4 is allocated to the cortical bone Co and the first nodes in the vicinity thereof. In addition, the label L5 is allocated to the cancellous bone Ca and the first nodes in the vicinity thereof.

As illustrated in FIG. 12, the medical image processing apparatus 30 sets the label L5 to some pixels in the region of the cancellous bone Ca in step S13, so that the label L5 can be allocated even in a thin region of the cancellous bone Ca. That is, even in a thin region such as cancellous bone Ca or a blood vessel, the medical image processing apparatus 30 according to the present embodiment can allocate the identification information to the thin region such as cancellous bone Ca or the blood vessel by setting the identification information to some pixels of the region and solving the shortest path problem once with the Dijkstra method, and can perform region extraction.

Next, as illustrated in FIG. 5, the medical image processing apparatus 30 outputs the medical image for which region extraction has been performed (step S23). The processing of outputting the medical image for which region extraction has been performed is realized by the generation function 35e in the processing circuitry 35. Specifically, the medical image processing apparatus 30 outputs the medical image for which region extraction has been performed by allocating the identification information to the first node for which the identification information is not set in step S21. More specifically, the medical image processing apparatus 30 according to the present embodiment displays the medical image for which region extraction has been performed on the display 32.

By executing step S23, the region extraction processing according to the present embodiment is ended.

As described above, in the medical image processing system 1 according to the present embodiment, the medical image processing apparatus 30 acquires a medical image, determines a plurality of seed points in the medical image, selects one of the plurality of seed points on the shortest path from the first node that is a pixel of the medical image for which identification information has not been set, and allocates the identification information set for the seed point on the shortest path from the first node to the first node based on the selection result. Therefore, it is possible to perform region extraction with a plurality of labels in a short time without requiring a large amount of time in the region extraction with the plurality of labels.

Note that, in the above-described embodiment, the medical image of the abdomen has been described as an example, but the imaging site in the medical image is not limited to the abdomen. That is, the imaging site in the medical image is arbitrary, and for example, the imaging site in the medical image may be the brain, the spine, or a lung.

Furthermore, in a case where the imaging site is the brain, the region extracted in the region extraction processing may be the cerebral artery or the cerebral vein. That is, the medical image processing apparatus 30 may perform region extraction of the cerebral artery and the cerebral vein. Furthermore, in a case where the imaging site is the spine, the region extracted in the region extraction processing may be each vertebral body in the spine. That is, the medical image processing apparatus 30 may perform region extraction of each vertebral body in the spine. Furthermore, in a case the imaging site is the lung, the region extracted in the region extraction processing may be a pulmonary artery and a pulmonary vein. That is, in a case where the imaging site is the lung, the medical image processing apparatus 30 may perform region extraction of the pulmonary artery and the pulmonary vein.

Furthermore, in a case where the region extraction of the cerebral artery and the cerebral vein and the region extraction of the pulmonary artery and the pulmonary vein are performed, the medical image processing apparatus 30 may apply the energy of the first edge based on the likelihood related to the cerebral artery connection, the cerebral vein connection, the pulmonary artery connection or the pulmonary vein connection when generating the graph structure in step S17. Furthermore, the likelihood related to the cerebral artery connection, the cerebral vein connection, the pulmonary artery connection or the pulmonary vein connection may be selected with a weight determined by deep learning.

Furthermore, in step S13, the medical image processing apparatus 30 may extract a specific region in the medical image and determine a plurality of seed points in the medical image based on the specific region. Here, the specific region is a region that can be specified in the medical image, and is, for example, a blood vessel region, a vertebral body region, or the like included in the medical image. As described above, the medical image processing apparatus 30 can reduce the number of first nodes to which identification information is not allocated by extracting the specific region, and thus, it is possible to reduce the time required for selecting the shortest path.

In addition, in step S15, the medical image processing apparatus 30 sets the range to which the identification information is allocated for all the pixels in the medical image, but the range to which the identification information is allocated is not limited thereto. For example, in a case where the specific region is extracted in the medical image in step S13, the pixels included in the specific region may be used as the range to which the identification information is allocated.

In addition, in step S13, the medical image processing apparatus 30 may execute filter processing for emphasizing the outline of each of the plurality of regions by the filter processing function 35f for emphasizing the outline of each of the plurality of regions in the medical image. In a case where this filter processing is executed, in step S17, the medical image processing apparatus 30 does not connect the pixel inside each of the plurality of regions in which the outline is emphasized and the pixel outside each of the plurality of regions in which the outline is emphasized with the first edge. That is, the medical image processing apparatus 30 generates a graph structure with the outline of each of the plurality of regions emphasized by the filter processing as a boundary. As a result, when selecting the shortest path from the start point to the first node in step S19, the medical image processing apparatus 30 prevents a path between the pixel inside each of the plurality of regions in which the outline is emphasized and the pixel outside each of the plurality of regions in which the outline is emphasized from being passed. As described above, by not passing through the path between the pixel inside each of the plurality of regions in which the outline is emphasized and the pixel outside each of the plurality of regions in which the outline is emphasized, an accuracy of the region extraction can be enhanced.

Note that the medical image processing apparatus 30 does not connect, with the first edge, between the pixel inside each of the plurality of regions in which the outline is emphasized and the pixel outside each of the plurality of regions in which the outline is emphasized in a case where the outline of each of the plurality of regions is emphasized, but in a case where the outline of each of the plurality of regions is emphasized, the medical image processing apparatus 30 may determine that a difference between the pixel inside each of the plurality of regions in which the outline is emphasized and the pixel outside each of the plurality of regions in which the outline is emphasized is large and increase energy applied to the first edge between the pixel inside each of the plurality of regions in which the outline is emphasized and the pixel outside each of the plurality of regions in which the outline is emphasized.

Note that the word "processor" used in above descriptions means circuits such as, for example, a Central Processing Unit (CPU), a Graphics Processing Unit (GPU), an Application Specific Integrated Circuit (ASIC), a programmable logic device (for example, a Simple Programmable Logic Apparatus (SPLD), a Complex Programmable Logic Apparatus (CPLD), and a Field Programmable Gate Array (FPGA)). The processor executes functions by reading and executing programs stored in the memory 31. Note that programs may be configured to be directly integrated in the processor instead of being storing in the memory 31. In this case, the processor realizes functions by reading and executing programs stored in the circuit. Note that the processor is not limited to the case arranged as a single processor circuit, but may be configured as a single processor by combining a plurality of independent circuits to realize functions. Furthermore, a plurality of component elements in FIG. 2 may be integrated into one processor to realize the functions.

While certain embodiments have been described, these embodiments have been presented by way of example only and are not intended to limit the scope of the inventions. The embodiments may be in a variety of other forms. Furthermore, various omissions, substitutions and changes may be made without departing from the spirit of the inventions. The embodiments and their modifications are included in the scope and the subject matter of the invention, and at the same time included in the scope of the claimed inventions and their equivalents.

The invention claimed is:

1. A medical image processing apparatus, comprising:
   processing circuitry configured to:
   acquire a medical image for setting identification information for identifying a plurality of regions in the medical image;
   determine a plurality of seed points in the medical image;
   select one of the plurality of seed points on a shortest path from a first node, the shortest path being a path in which a sum of energies between pixels in the medical image is minimized, and the first node being a pixel of the medical image for which the identification information is not set; and
   allocate the identification information to the first node,
   wherein the processing circuitry is further configured to generate a graph structure including a plurality of first nodes and connecting the plurality of seed points and the plurality of first nodes,
   the graph structure further includes a second node provided outside the medical image and connected to the plurality of seed points, and
   the processing circuitry is further configured to select the shortest path from the second node to the first node, thereby selecting one of the plurality of seed points on the shortest path from the first node.

2. The medical image processing apparatus of claim 1, wherein the plurality of regions includes an anatomical structure of a human body.

3. The medical image processing apparatus of claim 1, wherein the graph structure includes a plurality of first edges connecting the plurality of seed points and the plurality of first nodes, and
   wherein the processing circuitry is further configured to apply energy to the plurality of first edges based on a difference between the pixels in the medical image.

4. The medical image processing apparatus of claim 3, wherein the processing circuitry is further configured to apply the energy to the plurality of first edges based on a difference in pixel values between the pixels in the medical image.

5. The medical image processing apparatus of claim 4, wherein the processing circuitry is further configured to apply the energy to the plurality of first edges based on a difference in existence probability between the pixels in the medical image, the existence probability being a probability that the pixel belongs to one of the plurality of regions.

6. The medical image processing apparatus of claim 1,
   wherein the graph structure includes a plurality of second edges connecting the plurality of seed points with the second node, and
   wherein the processing circuitry is further configured to apply a same energy to the plurality of second edges.

7. The medical image processing apparatus of claim 1, wherein the processing circuitry is further configured to:
   perform, on the medical image, filter processing of emphasizing an outline of each of the plurality of regions in the medical image; and
   generate the graph structure with, as a boundary, the outline of each of the plurality of regions emphasized by the filter processing.

8. The medical image processing apparatus of claim 4, wherein the processing circuitry is further configured to select the shortest path from the second node to the first node so that a sum of energies applied to the first edges from the second node to the first node is minimized, thereby selecting one of the plurality of seed points on the shortest path from the first node.

9. The medical image processing apparatus of claim 1, wherein the processing circuitry is further configured to select one of the plurality of seed points on the shortest path from the first node with a Dijkstra method.

10. The medical image processing apparatus of claim 1, wherein the processing circuitry is further configured to receive, from an operator, an input operation of determining the plurality of seed points in the medical image and determine the plurality of seed points in the medical image according to the input operation.

11. The medical image processing apparatus of claim 1, wherein the processing circuitry is further configured to determine the plurality of seed points in the medical image with a learned model machine-learned to determine the plurality of seed points in the medical image by receiving an input of the medical image.

12. The medical image processing apparatus of claim 1, wherein the processing circuitry is further configured to determine the plurality of seed points in the medical image based on a CT value of the medical image.

13. The medical image processing apparatus of claim 1, wherein the processing circuitry is further configured to extract a specific region in the medical image and determine the plurality of seed points in the medical image based on the specific region.

* * * * *